(12) United States Patent
Vincent et al.

(10) Patent No.: US 9,169,173 B2
(45) Date of Patent: Oct. 27, 2015

(54) LIQUID PHASE ALKYLATION PROCESS

(71) Applicant: ExxonMobil Chemical Patents Inc., Baytown, TX (US)

(72) Inventors: Matthew J. Vincent, Kingwood, TX (US); Terry E. Helton, Bethlehem, PA (US); Ivy D. Johnson, Lawrenceville, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/268,188

(22) Filed: May 2, 2014

(65) Prior Publication Data

US 2014/0243567 A1 Aug. 28, 2014

Related U.S. Application Data

(63) Continuation of application No. 13/594,554, filed on Aug. 24, 2012, now Pat. No. 8,816,145, which is a continuation-in-part of application No. 13/076,799, filed on Mar. 31, 2011, now Pat. No. 8,334,419, which is a continuation of application No. 12/835,180, filed on Jul. 13, 2010, now Pat. No. 7,939,700, which is a continuation of application No. 11/820,907, filed on Jun. 21, 2007, now Pat. No. 7,790,940.

(60) Provisional application No. 61/535,632, filed on Sep. 16, 2011.

(51) Int. Cl.
| | |
|---|---|
| *C07C 2/66* | (2006.01) |
| *C07C 6/12* | (2006.01) |
| *C07C 6/06* | (2006.01) |
| *B01J 29/70* | (2006.01) |
| *C10G 29/20* | (2006.01) |

(52) U.S. Cl.
CPC ............... *C07C 6/06* (2013.01); *B01J 29/7038* (2013.01); *C07C 2/66* (2013.01); *C10G 29/205* (2013.01); *B01J 2229/42* (2013.01); *C07C 2521/04* (2013.01); *C07C 2521/16* (2013.01); *C07C 2529/70* (2013.01); *C10G 2300/1092* (2013.01); *C10G 2300/1096* (2013.01); *C10G 2300/4006* (2013.01); *C10G 2300/4012* (2013.01); *C10G 2300/4018* (2013.01); *C10G 2400/30* (2013.01)

(58) Field of Classification Search
USPC .......................................... 585/467, 475, 323
See application file for complete search history.

(56) References Cited

U.S. PATENT DOCUMENTS

| | | | |
|---|---|---|---|
| 3,308,069 A | 3/1967 | Wadlinger et al. | |
| 3,354,078 A | 11/1967 | Miale et al. | |
| 3,449,070 A | 6/1969 | McDaniel et al. | |
| 3,751,504 A | 8/1973 | Keown et al. | |
| 3,766,093 A | 10/1973 | Chu | |
| 3,894,104 A | 7/1975 | Chang et al. | |
| 4,016,218 A | 4/1977 | Haag et al. | |
| 4,415,438 A | 11/1983 | Dean et al. | |
| 4,439,409 A | 3/1984 | Puppe et al. | |
| 4,459,426 A | 7/1984 | Inwood et al. | |
| 4,547,605 A | 10/1985 | Kresge et al. | |
| 4,826,667 A | 5/1989 | Zones et al. | |
| 4,891,458 A | 1/1990 | Innes et al. | |
| 4,954,325 A | 9/1990 | Rubin et al. | |
| 4,992,606 A | 2/1991 | Kushnerick et al. | |
| 5,051,387 A | 9/1991 | Koetsier et al. | |
| 5,149,894 A | 9/1992 | Holtermann et al. | |
| 5,236,575 A | 8/1993 | Bennett et al. | |
| 5,250,277 A | 10/1993 | Kresge et al. | |
| 5,334,795 A | 8/1994 | Chu et al. | |
| 5,362,697 A | 11/1994 | Fung et al. | |
| 5,557,024 A | 9/1996 | Cheng et al. | |
| 5,600,048 A | 2/1997 | Cheng et al. | |
| 5,600,050 A | 2/1997 | Huang et al. | |
| 5,827,491 A | 10/1998 | Emerson et al. | |
| 5,959,168 A | 9/1999 | Van der Aalst et al. | |
| 6,077,498 A | 6/2000 | Diaz Cabana et al. | |
| 6,231,751 B1 | 5/2001 | Canos et al. | |
| 6,376,730 B1 | 4/2002 | Jan et al. | |
| 6,710,003 B2 | 3/2004 | Jan et al. | |

(Continued)

FOREIGN PATENT DOCUMENTS

| | | |
|---|---|---|
| CN | 1500724 A | 6/2004 |
| CN | 101384368 | 3/2009 |

(Continued)

OTHER PUBLICATIONS

Corma et al., "*Infrared Spectroscopy, Thermoprogrammed Desorption, and Nuclear Magnetic Resonance Study of the Acidity, Structure, and Stability of Zeolite MCM-22*", Zeolites, vol. 15, pp. 576-582 (1995).

(Continued)

*Primary Examiner* — Thuan D Dang

(74) *Attorney, Agent, or Firm* — Darryl M. Tyrus

(57) ABSTRACT

The present invention provides a process for producing a monoalkylated benzene comprising the step of contacting benzene with an alkylating agent in the presence of a catalyst composition under effective alkylation conditions to form said monoalkylated benzene and polyalkylated benzene, said catalyst composition comprising MCM-56 and a binder, such that the crystal/binder weight ratio in said catalyst composition is from about 20/80 to about 80/20, wherein said polyalkylated benzene comprises dialkylated benzene and trialkylated benzene, and the weight ratio of trialkylated benzene to dialkylated benzene is in the range from about 0.08 to about 0.12.

18 Claims, 5 Drawing Sheets

(56) References Cited

U.S. PATENT DOCUMENTS

| | | |
|---|---|---|
| 6,756,030 B1 | 6/2004 | Rohde et al. |
| 6,864,203 B2 | 3/2005 | Hendriksen et al. |
| 6,936,744 B1 | 8/2005 | Cheng et al. |
| 6,984,764 B1 | 1/2006 | Roth et al. |
| 7,084,087 B2 | 8/2006 | Shan et al. |
| 7,396,969 B2 | 7/2008 | Cheng et al. |
| 7,790,940 B2 | 9/2010 | Clark et al. |
| 2002/0137977 A1 | 9/2002 | Hendriksen et al. |
| 2004/0138051 A1 | 7/2004 | Shan et al. |
| 2005/0197517 A1 | 9/2005 | Cheng et al. |
| 2011/0178353 A1 | 7/2011 | Clark et al. |

FOREIGN PATENT DOCUMENTS

| | | |
|---|---|---|
| CN | 101688130 | 3/2010 |
| CN | 103796953 | 5/2014 |
| EP | 0 293 032 | 11/1988 |
| EP | 0 847 802 | 6/1998 |
| JP | 05-502035 | 4/1993 |
| JP | 08-511544 | 12/1996 |
| JP | 11-199526 | 7/1999 |
| JP | 2002-506838 | 3/2002 |
| JP | 2002-532443 | 10/2002 |
| JP | 2003-509479 | 3/2003 |
| JP | 2004-534845 | 11/2004 |
| JP | 2005-507375 | 3/2005 |
| WO | WO 97/17290 | 5/1997 |
| WO | WO 98/03453 | 1/1998 |
| WO | WO 98/16468 | 4/1998 |
| WO | WO 2004/046034 | 6/2004 |
| WO | WO 2005/118476 | 12/2005 |
| WO | WO 2006/002805 | 1/2006 |
| WO | WO 2007/139629 | 12/2007 |
| WO | WO 2008/013644 | 1/2008 |
| WO | WO 2009/127533 | 10/2009 |

OTHER PUBLICATIONS

Kennedy et al., "*Multinuclear MAS NMR Studies of Zeolites MCM-22 and MCM-49*", Catalysis Today, vol. 49, pp. 385-399 (1999).

Lee et al., "*Reinvestigation Into the Synthesis of Zeolite Diquaternary Alkylammonium Ions $(CH_3)_3N^+ {}^($$CH_2)nN^+ (CH_3)_3$ With n=3–10 as Structure-Directing Agents*", Microporous and Mesoporous Materials, vol. 68, pp. 97-104 (2004).

Mochida et al., "*The Effects of Seeding in the Synthesis of Zeolite MCM-22 in the Presence of Hexamethyleneimine*", Zeolites, vol. 18, pp. 142-151 (1997).

Roth, "*MCM-22 Zeolite Family and the Delaminated Zeolite MCM-56 Obtained in One-Step Synthesis*", Studies in Surface Science and Catalysis, vol. 158, pp. 19-26 (2005).

Yang et al., "*Influence of Synthesis Method on the Properties and Catalytic Performance of MCM-49 Zeolites*", Catalysis Communications, vol. 8, pp. 997-1002 (2007).

*Atlas of Zeolite Framework Types*, 2001.

LIQUID PHASE ALKYLATION PROCESS

CROSS REFERENCE TO RELATED APPLICATIONS

This application is a continuation of U.S. application Ser. No. 13/594,554, filed Aug. 24, 2012, now U.S. Pat. No. 8,816, 145; which is a continuation-in-part of U.S. application Ser. No. 13/076,799, filed Mar. 31, 2011, now U.S. Pat. No. 8,334, 419; which is a continuation of U.S. application Ser. No. 12/835,180, filed Jul. 13, 2010, now U.S. Pat. No. 7,939,700; which is a continuation of U.S. application Ser. No. 11/820, 907, filed Jun. 21, 2007, now U.S. Pat. No. 7,790,940, the disclosures of which are fully incorporated herein by reference in their entireties. U.S. application Ser. No. 13/594,554 claims the benefit of U.S. Provisional Application No. 61/535,632, filed Sep. 16, 2011, and priorities to EP 11188529.9, filed Nov. 10, 2011, and International Application No. PCT/US2012/51181, filed Aug. 16, 2012, the disclosures of which are fully incorporated by reference in their entireties.

BACKGROUND

The present invention relates to an improved process for producing alkylaromatics, for example, ethylbenzene, cumene and sec-butylbenzene.

Of the alkylaromatic compounds advantageously produced by the present improved process, ethylbenzene and cumene, for example, are valuable commodity chemicals which are used industrially for the production of styrene monomer and coproduction of phenol and acetone respectively. In fact, a common route for the production of phenol comprises a process which involves alkylation of benzene with propylene to produce cumene, followed by oxidation of the cumene to the corresponding hydroperoxide, and then cleavage of the hydroperoxide to produce equimolar amounts of phenol and acetone. Ethylbenzene may be produced by a number of different chemical processes. One process which has achieved a significant degree of commercial success is the vapor phase alkylation of benzene with ethylene in the presence of a solid, acidic ZSM-5 zeolite catalyst. Examples of such ethylbenzene production processes are described in U.S. Pat. No. 3,751,504 (Keown), U.S. Pat. No. 4,547,605 (Kresge) and U.S. Pat. No. 4,016,218 (Haag).

Another process which has achieved significant commercial success is the liquid phase process for producing ethylbenzene from benzene and ethylene since it operates at a lower temperature than the vapor phase counterpart and hence tends to result in lower yields of by-products. For example, U.S. Pat. No. 4,891,458 (Innes) describes the liquid phase synthesis of ethylbenzene with zeolite beta, whereas U.S. Pat. No. 5,334,795 (Chu) describes the use of MCM-22 in the liquid phase synthesis of ethylbenzene. The latter patent teaches use of catalyst comprising MCM-22 crystalline material and binder in the ratio of crystal/binder of from about 1/99 to about 90/10.

Cumene has for many years been produced commercially by the liquid phase alkylation of benzene with propylene over a Friedel-Craft catalyst, particularly solid phosphoric acid or aluminum chloride. More recently, however, zeolite-based catalyst systems have been found to be more active and selective for propylation of benzene to cumene. For example, U.S. Pat. No. 4,992,606 (Kushnerick) describes the use of MCM-22 in the liquid phase alkylation of benzene with propylene.

Other publications show use of catalysts comprising crystalline zeolites and binders for conversion of feedstock comprising an alkylatable aromatic compound and an alkylating agent to alkylaromatic conversion product under at least partial liquid phase conversion conditions. These include U.S. 2005/0197517A1 (Cheng) showing use of a catalyst crystal/binder ratio of 65/35 and 100/0; U.S. 2002/0137977A1 (Hendriksen) showing use of a catalyst crystal/binder ratio of 100/0 while noting the perceived negative effect of binders on selectivity; U.S. 2004/0138051A1 (Shan) showing use of a catalyst comprising a microporous zeolite embedded in a mesoporous support, where the zeolite/support ratio is from less than 1/99 to more than 99/1, preferably from 3/97 to 90/10; WO 2006/002805 (Spano) teaching use of a catalyst crystal/binder ratio of 20/80 to 95/5, exemplifying 55/45; U.S. Pat. No. 6,376,730 (Jan) showing use of layered catalyst crystal/binder of 70/30 and 83/17; European Patent No. 0847802B1 showing use of a catalyst crystal/binder ratio of from 50/50 to 95/5, preferably from 70/30 to 90/10; and U.S. Pat. No. 5,600,050 (Huang) showing use of catalyst comprising 30 to 70 wt. % H-Beta zeolite, 0.5 to 10 wt. % halogen, and the remainder alumina binder.

Existing alkylation processes for producing alkylaromatic compounds, for example, ethylbenzene and cumene, inherently produce polyalkylated species as well as the desired monoalkylated product. It is therefore normal to transalkylate the polyalkylated species with additional aromatic feed, for example benzene, to produce additional monoalkylated product, for example ethylbenzene or cumene, either by recycling the polyalkylated species to the alkylation reactor or, more frequently, by feeding the polyalkylated species to a separate transalkylation reactor. Examples of catalysts which have been used in the alkylation of aromatic species, such as alkylation of benzene with ethylene or propylene, and in the transalkylation of polyalkylated species, such as polyethylbenzenes and polyisopropylbenzenes, are listed in U.S. Pat. No. 5,557,024 (Cheng) and include MCM-49, MCM-22, PSH-3, SSZ-25, zeolite X, zeolite Y, zeolite Beta, acid dealuminized mordenite and TEA-mordenite. Transalkylation over a small crystal (<0.5 micron) form of TEA-mordenite is also disclosed in U.S. Pat. No. 6,984,764.

Where the alkylation step is performed in the liquid phase, it is also desirable to conduct the transalkylation step under liquid phase conditions. However, by operating at relatively low temperatures, liquid phase processes impose increased requirements on the catalyst, particularly in the transalkylation step where the bulky polyalkylated species must be converted to additional monoalkylated product without producing unwanted by-products. This has proven to be a significant problem in the case of cumene production where existing catalysts have either lacked the desired activity or have resulted in the production of significant quantities of by-products such as ethylbenzene and n-propylbenzene.

Although it is suggested in the art that catalysts for conversion of feedstock comprising an alkylatable aromatic compound and an alkylating agent to alkylaromatic conversion product under at least partial liquid phase conversion conditions are composed of a porous crystalline aluminosilicate and binder in the ratio of crystal/binder of from 1/99, e.g., 5/95, to 100/0, current commercial catalysts, i.e. those found to be commercially useful, for this process are composed of a porous crystalline aluminosilicate and binder in the ratio of crystal/binder of either 65/35 or 80/20. Finding a commercially acceptable catalyst for such processes conducted under at least partial liquid phase conversion conditions which increases monoselectivity, i.e. lower di- or polyalkyl product make, would allow capacity expansion in existing plants and lower capital expense for grassroots plants as a result of lower aromatic compound/alkylating agent ratios.

U.S. Published Patent Application No. 2011/0178353 to Clark et al. discloses a liquid phase or partial liquid phase alkylation process for producing alkylaromatics conducted in the presence of a specific catalyst comprising a porous crystalline material, e.g., a crystalline aluminosilicate, ("crystal") and binder in the ratio of crystal/binder of from about 20/80 to about 60/40, which yields a unique combination of activity and, importantly, monoselectivity. Suitable catalysts disclosed to include the MCM-22 family materials.

The MCM-22 family molecular sieves have been found to be useful in a variety of hydrocarbon conversion processes. Examples of MCM-22 family molecular sieve are MCM-22, MCM-49, MCM-56, ITQ-1, ITQ-2, PSH-3, SSZ-25, ERB-1, UZM-8, and UZM-8HS. In particular, MCM-56 is a layered oxide material, rather than a three dimensionally ordered zeolite, in which each layer in MCM-56 is porous and has a framework structure closely related to that of MCM-22 and other MCM-22 family materials.

U.S. Provisional Application No. 61/535,632 to Johnson et al., filed Sep. 12, 2011 and incorporated herein by reference in its entirety, discloses an improved method for manufacturing high quality porous seeded-crystalline MCM-56 material by incorporating MCM-56 seed crystals into the initial reaction mixture. It also relates to the seeded-MCM-56 material manufactured by the improved method, catalyst compositions comprising same and use thereof in a process for catalytic conversion of hydrocarbon compounds.

According to the present invention, it has now unexpectedly been found that a seeded-MCM-56 crystalline aluminosilicate in combination with a binder in the crystal/binder weight ratio of from above about 20/80 to about 80/20, preferably from about 40/60 to about 60/40, yields a unique combination of activity and, importantly, monoselectivity in liquid phase or partial liquid phase alkylation processes for producing alkylaromatics.

SUMMARY

According to the present invention, there is provided an improved process for producing a monoalkylated benzene comprising the step of contacting benzene with an alkylating agent in the presence of a catalyst composition under effective alkylation conditions to form said monoalkylated benzene and polyalkylated benzene, said catalyst composition comprising MCM-56 and a binder, such that the crystal/binder weight ratio in said catalyst composition is from about 20/80 to about 80/20, wherein said polyalkylated benzene comprises dialkylated benzene and trialkylated benzene, and the weight ratio of trialkylated benzene to dialkylated benzene is in the range from about 0.08 to about 0.12.

In one or more embodiments, the improved process further comprising the step of contacting said polyalkylated benzene with additional benzene in the presence of a transalkylation catalyst to produce additional monoalkylated benzene.

DETAILED DESCRIPTION OF THE INVENTION

Figure 1:
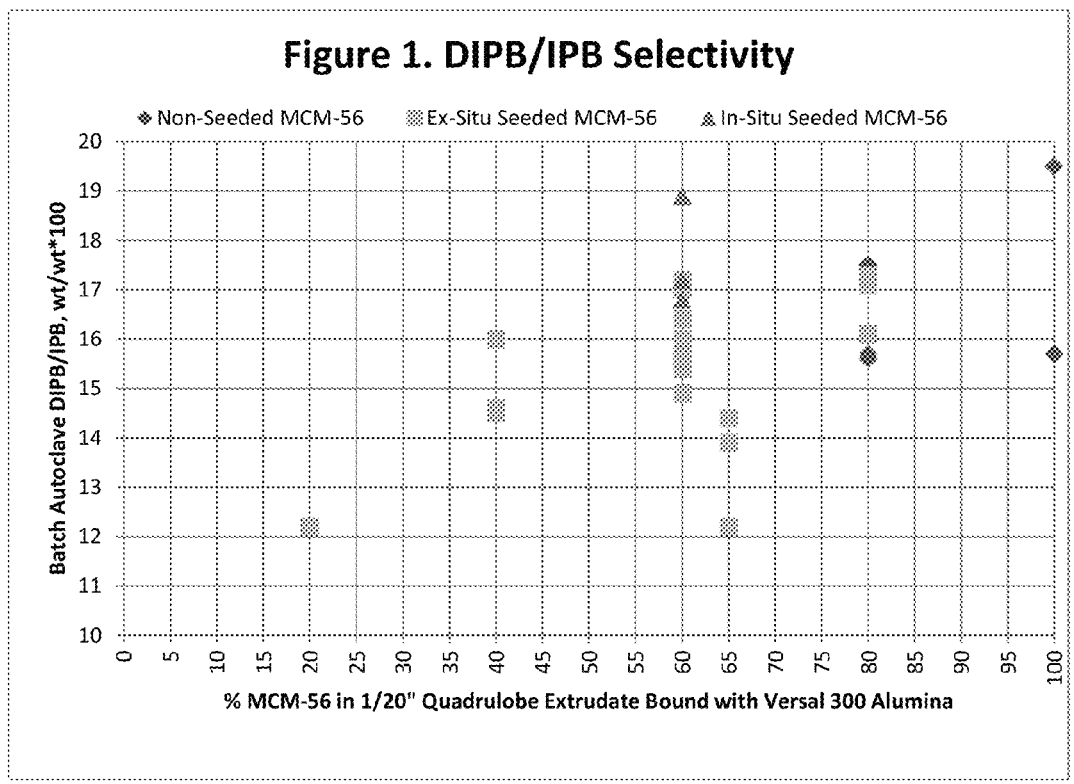
FIG. 1 shows a plot of diisopropylbenzene/isopropylbenzene selectivity (ordinate) versus the percentage of MCM-56 in the 1/20" quadrulobe extrudate bound with Versal 300 alumina, for non-seeded MCM-56 (abscissa), ex-situ seeded MCM-56 and in-situ seeded MCM-56.

The present invention relates to an improved process for production of monoalkylated aromatic compounds, particularly ethylbenzene, cumene and sec-butylbenzene, by the liquid or partial liquid phase alkylation of an alkylatable aromatic compound, particularly benzene. More particularly, the present process uses a catalyst composition comprising a porous crystalline material, e.g., a crystalline aluminosilicate, and binder at a crystal/binder weight ratio of from above about 20/80 to about 80/20, or from above about 20/80 to about 60/40, preferably from about 20/80 to about 40/60, or even more preferably from about 40/60 to about 60/40.

Methods for producing the catalysts required for use in the present invention comprise those taught in the publications listed below and incorporated herein by reference, modified only by adjusting the compounding or extrusion, for example, of the final catalyst to comprise a crystal/binder ratio of from about 20/80 to about 60/40. This is well within the ability of those skilled in catalyst manufacturing art. For example, U.S. Pat. No. 4,954,325 describes crystalline MCM-22 and catalyst comprising same, U.S. Pat. No. 5,236,575 describes crystalline MCM-49 and catalyst comprising same, and U.S. Pat. Nos. 5,362,697 and 5,557,024 describe crystalline MCM-56 and catalyst comprising same. In compounding or extruding the particular crystalline material with binder to form the catalyst required for use herein, care is taken to do so such that the final catalyst product comprises a crystal/binder ratio of from about 20/80 to about 60/40 or from above about 20/80 to about 80/20, preferably from about 40/60 to about 80/20, or even more preferably from about 40/60 to about 60/40.

The term "ex-situ seeded" as used herein refers to a method for introducing zeolite seeds into a zeolite synthesis reactor in which zeolite seeds in their as-synthesized condition are added to the reactor.

The term "in-situ seeded" as used herein refers to a method for introducing zeolite seeds into a zeolite synthesis reactor in which residual zeolite seeds in their as-synthesized condition remain in the reactor from a previous zeolite crystallization.

The term "aromatic" in reference to the alkylatable aromatic compounds which may be useful as feedstock herein is to be understood in accordance with its art-recognized scope. This includes alkyl substituted and unsubstituted mono- and polynuclear compounds. Compounds of an aromatic character that possess a heteroatom are also useful provided they do not act as catalyst poisons under the reaction conditions selected.

Substituted aromatic compounds that can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction. Substituted aromatic compounds include polyalkylated aromatic compounds, such as dialkylated and trialkylated aromatic compounds.

Suitable aromatic compounds include benzene, naphthalene, anthracene, naphthacene, perylene, coronene, and phenanthrene, with benzene being preferred.

Generally the alkyl groups that can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, n-propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic compounds can also be used as starting materials and include aromatic organics such as are produced by the alkylation of aromatic organics with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing a mixture of benzene, toluene and/or xylene constitutes a particularly useful feed for the alkylation process of this invention.

The alkylating agents that may be useful in the process of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth. Polyalkylated aromatic compounds, such as dialkylated and trialkylated aromatic compounds, having one or more available alkylating aliphatic groups capable of reaction with the alkylatable aromatic compound, may serve as suitable alkylating agents in one or more embodiments of this invention.

Mixtures of light olefins are useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition in Table 3A below:

TABLE 3A

|  | Wt. % | Mole % |
| --- | --- | --- |
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products that may be obtained from the process of the present invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butene. Particularly preferred process mechanisms of the invention relate to the production of cumene by the alkylation of benzene with propylene, and production of ethylbenzene by the alkylation of benzene with ethylene.

The reactants for the present improved process can be in partially or completely liquid phase and can be neat, i.e., free from intentional admixture or dilution with other material, or they can be brought into contact with the catalyst composition with the aid of carrier gases or diluents such as, for example, hydrogen or nitrogen.

The improved alkylation process of this invention may be conducted such that the reactants, i.e., the alkylatable aromatic compound and the alkylating agent, are brought into contact with the present catalyst in a suitable reaction zone such as, for example, in a flow reactor containing a fixed bed of the catalyst composition, under effective alkylation conditions. Such conditions include a temperature of from about 0° C. to about 500° C., preferably from about 10° C. to about 260° C., a pressure of from about 0.2 to about 25,000 kPa-a, preferably from about 100 kPa-a to about 5500 kPa-a, a molar ratio of alkylatable aromatic compound to alkylating agent of from about 0.1:1 to about 50:1, preferably from about 0.5:1 to about 10:1, and a feed weight hourly space velocity (WHSV) based on the alkylating agent of from about 0.1 hr$^{-1}$ to 500 hr$^{-1}$, preferably from about 0.5 hr$^{-1}$ to about 100 hr$^{-1}$.

When benzene is alkylated with ethylene to produce ethylbenzene, the alkylation reaction is preferably carried out under at least partially liquid phase conditions, that is such that at least part of the benzene is in the liquid phase during the alkylation reaction. Suitable conditions include a temperature of from about 150° C. to about 300° C., more preferably from about 170° C. to about 260° C.; a pressure up to about 20,400 kPa-a, more preferably from about 2000 kPa-a to about 5500 kPa-a; a weight hourly space velocity (WHSV) based on the ethylene alkylating agent of from about 0.1 to about 20 hr$^{-1}$, more preferably from about 0.5 to about 6 hr$^{-1}$; and a ratio of benzene to ethylene in the alkylation reactor of from about 0.5:1 to about 30:1 molar, more preferably from about 1:1 to about 10:1 molar.

When benzene is alkylated with propylene to produce cumene, the reaction may also take place under at least partially liquid phase conditions including a temperature of up to about 250° C., preferably up to about 150° C., e.g., from about 10° C. to about 125° C.; a pressure of about 25,000 kPa-a or less, e.g., from about 100 kPa-a to about 3,000 kPa-a; a weight hourly space velocity (WHSV) based on propylene alkylating agent of from about 0.1 hr$^{-1}$ to about 250 hr$^{-1}$, preferably from about 1 hr$^{-1}$ to about 50 hr$^{-1}$; and a ratio of benzene to propylene in the alkylation reactor of from about 0.5:1 to about 30:1 molar, more preferably from about 1:1 to about 10:1 molar.

When benzene is alkylated with butenes, e.g., n-butene, to produce butylbenzene, e.g. sec-butylbenzene, the reaction may also take place under at least partially liquid phase conditions including a temperature of up to about 250° C., preferably up to about 150° C., e.g., from about 10° C. to about 125° C.; a pressure of about 25,000 kPa-a or less, e.g., from about 100 kPa-a to about 3,000 kPa-a; a weight hourly space velocity (WHSV) based on butenes alkylating agent of from about 0.1 hr$^{-1}$ to about 250 hr$^{-1}$, preferably from about 1 hr$^{-1}$ to about 50 hr$^{-1}$; and a ratio of benzene to butenes in the alkylation reactor of from about 0.5:1 to about 30:1 molar, more preferably from about 1:1 to about 10:1 molar.

The crystal portion of the catalyst for use in the present invention may comprise a crystalline molecular sieve having the structure of zeolite Beta (described in U.S. Pat. No. 3,308, 069) or an MCM-22 family material. The catalyst must include the crystalline molecular sieve combined in a conventional manner with an oxide binder as hereinafter detailed in the weight ratio of crystal/binder of from about 20/80 to about 80/20 or from above about 20/80 to about 40/60, preferably from about 20/80 to about 40/60, or even more preferably from about 40/60 to about 60/40.

For certain applications of the catalyst, the average particle size of the crystalline molecular sieve component may be from about 0.05 microns to about 200 microns, for example, from 20 microns to about 200 micron.

The term "MCM-22 family material" (or "material of the MCM-22 family" or "molecular sieve of the MCM-22 family"), as used herein, includes:
(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;
(ii) molecular sieves made from a common second degree building block, a 2-dimensional tiling of such MWW framework type unit cells, forming a "monolayer of one unit cell thickness", preferably one c-unit cell thickness;
(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof; or
(iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439, 409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697), and UZM-8 (described in U.S. Pat. No. 6,756,030). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

In particular, the molecular sieve employed in the present alkylation process comprises MCM-56 crystals produced by a process in which the synthesis mixture comprises seeds of zeolite crystals, especially MCM-56 crystals. A suitable process is disclosed in U.S. Provisional Application No. 61/535, 632 to Johnson et al, filed Sep. 16, 2011 and incorporated herein by reference in its entirety. The crystals so-manufactured are characterized herein as seeded MCM-56 crystals.

The seeded MCM-56 crystals are characterized by the X-ray diffraction pattern as disclosed in U.S. Pat. Nos. 5,362, 697 and 5,827,491, each patent incorporated herein by reference.

The X-ray diffraction pattern disclosed in U.S. Pat. Nos. 5,362,697 and 5,827,491 is shown below in Table 1 (as-synthesized) and Table 2 (as-calcined). In Tables 1 and 2, the intensities are defined relative to the d-spacing line at 12.4 Angstroms.

TABLE 1

| Interplanar d-Spacing (Angstroms) | Relative Intensity |
|---|---|
| 12.4 ± 0.2 | vs |
| 9.9 ± 0.3 | m |
| 6.9 ± 0.1 | w |
| 6.4 ± 0.3 | w |
| 6.2 ± 0.1 | w |
| 3.57 ± 0.07 | m-s |
| 3.44 ± 0.07 | vs |

TABLE 2

| Interplanar d-Spacing (Angstroms) | Relative Intensity |
|---|---|
| 12.4 ± 0.2 | vs |
| 9.9 ± 0.3 | m |
| 6.9 ± 0.1 | w |
| 6.2 ± 0.1 | w |
| 3.55 ± 0.07 | m-s |
| 3.42 ± 0.07 | vs |

The above X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d-spacings, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60-100), s=strong (40-60), m=medium (20-40) and w=weak (0-20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history.

The method for producing seeded MCM-56 crystals comprises the steps of:
a) preparing a first reaction mixture containing sources of alkali or alkaline earth metal (M), e.g., sodium or potassium, cation, an oxide of a trivalent element X, e.g., aluminum, an oxide of a tetravalent element Y, e.g., silicon, preferably, containing at least 30 wt. % of solid $YO_2$, and water, said first reaction mixture having a composition in terms of mole ratios of oxides, preferably, selected within the following ranges in Table 3B below:

TABLE 3B

| |
|---|
| $YO_2/X_2O_3$ = 5 to 35, e.g., 15 to 20; |
| $H_2O/YO_2$ = 10 to 70, e.g., 15 to 20; |
| $OH^-/YO_2$ = 0.05 to 0.20, e.g., 0.1 to 0.15; |
| $M/YO_2$ = 0.05 to 3.0, e.g., 0.11 to 0.15; | said first reaction mixture further comprising zeolite seed crystals, preferably, MCM-56 seed crystals, in an amount from greater than or equal to 0.05 wt. %, or greater than or equal to 0.10 wt. %, or greater than or equal to 0.50 wt. %, or greater than or equal to 1.0 wt. %, to less than or equal to 5 wt. %, e.g., greater than or equal to 1 to less than or equal to 3 wt. %, based on the weight of the first reaction mixture;

b) adding directing agent R, e.g., preferably, hexamethyleneimine (HMI), to the reaction mixture of step a) to form a second reaction mixture having said directing agent R in terms of a mole ratio within the following range: $R/YO_2$=0.08 to 0.3, e.g., 0.1 to 0.2;

c) crystallizing the second reaction mixture of step b) under conditions of a temperature of from about 90° C. to about 175° C., preferably, from about 90° C. to less than 160° C., e.g., from about 125° C. to about 175° C., and a time for less than 90 hours, preferably, for less than 40 hours, e.g., from about 20 hours to about 75 hours, at a stir rate of from about 40 rpm to about 250 rpm, preferably, from about 40 rpm to about 100 rpm, to form a resulting mixture comprising crystals of said MCM-56 material and less than or equal to 10 wt. %, e.g., less than or equal to about 5 wt. %, of non-MCM-56 impurity crystals, based on the total weight of said MCM-56 crystals in said second reaction mixture, as identified by X-ray diffraction, such as, for example, crystalline MCM-22 family materials (defined below), such as MCM-49 material, or ferrierite, kenyaite or mixtures thereof; and d) separating and recovering at least a portion of crystals of said MCM-56 material from the resulting mixture of step c) to form as-synthesized MCM-56 material wherein said crystals of as-synthesized MCM-56 material is characterized by the X-ray diffraction pattern shown in Table 1 above.

The second reaction mixture of step b) has a solids content of range from at least 12 wt. %, or at least 15 wt. %, or at least 18 wt. %, or at least 20 wt. %, or at least 30 wt. % up to less than 40 wt. %, or less than 50 wt. %, or less than 60 wt. %, based on the weight of the second reaction mixture. Preferably, the solids content of the second reaction mixture of step b) is less than 30 wt. %, based on the weight of the second reaction mixture.

In order to achieve the required first reaction mixture composition for this improved method, some selective critical changes have to be made to the method for making MCM-56 material as compared to the current practice. For example, the addition of caustic NaOH is eliminated, except as a component of, for example, sodium aluminate. Also, the organic directing agent is not added to the first reaction mixture during its formation, but a controlled amount of organic directing agent reduced to nearly stoichiometric amounts is only added to the fully formed first reaction mixture to form the second reaction mixture. Further, zeolite seeds crystals, preferably, zeolite seed crystals of MCM-22 family material, more preferably, zeolite seed crystals of MCM-56, are added to the first reaction mixture based on its total weight such that the amount of seed crystals is from greater than or equal to 0.05 wt. %, or greater than or equal to 0.10 wt. %, or greater than or equal to 0.50 wt. %, or greater than or equal to 1.0 wt. %, to less than or equal to 5 wt. %, e.g., from greater than or equal to 1 to less than or equal to 3 wt. %, of the first reaction mixture. Surprisingly, adding MCM-56 seed crystals to the first reaction mixture required for this improved method does not accelerate the formation of impurities as would normally be expected in such a crystallization procedure.

The improved method of this invention beneficially stabilizes and extends the crystallization window in step c) of the method to avoid impurity, e.g., MCM-49 material, formation; reduces organic loading in the crystallization step c) lowering cost, especially important in commercial MCM-56 manufacturing; and accelerates the crystallization rate in step c) to greatly improve throughput. Further, the intentional addition of the preferred MCM-56 seed crystals swamps out normally expected effects of acceleration of crystallization of impurities caused by residual particles in the crystallizer. This is especially important in commercial manufacturing. In the improved method, seeding did not accelerate the introduction of impurities.

In the present improved method, the source of $YO_2$ must comprise solid $YO_2$, for example at least about 30 wt. % solid $YO_2$. When $YO_2$ is silica, the use of a silica source containing at least about 30 wt. % solid silica, e.g., Ultrasil, now known as Sipernat® (a precipitated, spray dried silica containing about 90 wt. % silica) or HiSil™ (a precipitated hydrated silica containing about 87 wt. % silica, about 6 wt. % free $H_2O$ and about 4.5 wt. % bound $H_2O$ of hydration and having a particle size of about 0.02 micron) favors crystalline MCM-56 formation from the above second reaction mixture under the synthesis conditions required. Preferably, therefore, the $YO_2$, e.g., silica, source contains at least about 30 wt. % solid $YO_2$, e.g., silica, and more preferably at least about 40 wt. % solid $YO_2$, e.g., silica.

Organic directing agent R may be selected from the group consisting of cycloalkylamine, azacycloalkane, diazacycloalkane, and combinations thereof, alkyl comprising from 5 to 8 carbon atoms. Non-limiting examples of R include cyclopentylamine, cyclohexylamine, cycloheptylamine, hexamethyleneimine (HMI), heptamethyleneimine, homopiperazine, and combinations thereof.

It is noted that the reaction mixture components can be supplied by more than one source. The reaction mixture can be prepared either batchwise or continuously.

Step c) crystallization of the second reaction mixture in the present method is preferably carried out under stirred conditions in a suitable reactor vessel, such as for example, polypropylene containers or Teflon lined or stainless steel autoclaves. However, it is within the scope of this invention for crystallization to occur under static conditions.

The useful ranges of conditions for crystallization in this method are a temperature from about 90° C. to about 175° C., preferably, from about 90° C. to less than 160° C., e.g., from about 125° C. to about 175° C., and a time for less than 90 hours, preferably, for less than 40 hours, e.g., from about 20 hours to about 75 hours, preferably, at a stir rate of from about 40 rpm to about 250 rpm, more preferably, from about 40 rpm to about 100 rpm, to form a resulting mixture comprising high quality crystals of MCM-56 material and less than or equal to 10 wt. % non-MCM-56 impurity crystals, based on the total weight of said MCM-56 crystals recovered from the reaction mixture, as identified by X-ray diffraction. Thereafter, the crystals of as-synthesized MCM-56 material are separated from the resulting liquid mixture and recovered in step d).

Another embodiment of the improved method comprises aging the second reaction mixture of step b) prior to crystallizing step c) for from about 0.5 to about 48 hours, for example from about 0.5 to about 24 hours, at a temperature of from about 25° C. to about 75° C. Preferably, the second reaction mixture was agitated with stirring at, for example 50 rpm, for less than 48 hours at ambient temperature.

Catalyst comprising the seeded MCM-56 material manufactured hereby may be used to effect conversion in chemical reactions, and is particularly useful in a process for selectively producing a desired monoalkylated aromatic compound comprising the step of contacting an alkylatable aromatic compound with an alkylating agent in the presence of the catalyst under at least partial liquid phase conditions. Another aspect of the present invention, therefore, is an improved alkylation catalyst comprising the high quality seeded MCM-56 manufactured by the present improved method for use in a process for the selective production of a product comprising monoalkylated benzene, the process comprising the step of reacting benzene with an alkylating agent, such as ethylene or propylene, under alkylation conditions in the presence of said alkylation catalyst to form said product. Using the present catalyst as an alkylation catalyst to effect alkylation of an alkylatable aromatic compound, the alkylating agent may include an alkylating aliphatic group having 1 to 5 carbon atoms. The alkylating agent may be, for example, ethylene or propylene and the alkylatable aromatic compound in such an instance may suitably be benzene.

In one or more embodiments of the process for the selective production of monoalkylated benzene, the product may further comprise formation of polyalkylated benzene which comprises dialkylated benzene and trialkylated benzene. In such case, the weight ratio of the trialkylated benzene to dialkylated benzene is in the range from 0.02 to 0.16, or from 0.4 to 0.16, or from 0.08 to 0.12.

The MCM-56 manufactured hereby may be used as a catalyst component to effect hydrocarbon compound conversion, and is particularly useful as catalyst in a process for selectively producing ethylbenzene or cumene, the process comprising the step of contacting benzene with ethylene or propylene under at suitable alkylation conditions, such as at least partial liquid phase conditions.

The catalyst for use in the alkylation process of the present invention will include an inorganic oxide material matrix or binder. Such matrix or binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful catalyst matrix or binder materials employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

In the present process of making ethylbenzene from benzene and ethylene, the relative proportions of the seeded MCM-56 crystals and binder or matrix may vary narrowly with the ratio of crystal/binder of from above about 20/80 to about 80/20, preferably from about 40/60 to about 80/20, or even from about 40/60 to 60/40.

In the process of the present invention, the alkylation reactor effluent may contain excess aromatic feed, monoalkylated product, polyalkylated products (e.g., polyalkylated benzene), and various impurities. The aromatic feed is recovered by distillation and recycled to the alkylation reactor. Usually a small bleed is taken from the recycle stream to eliminate unreactive impurities from the loop. The bottoms from the distillation may be further distilled to separate monoalkylated product from polyalkylated products and other heavies.

The polyalkylated products separated from the alkylation reactor effluent is a suitable alkylating agent which may be reacted with additional aromatic feed (as an alkylatable aromatic compound) in a transalkylation reactor, separate from the alkylation reactor, over a suitable transalkylation catalyst. The transalkylation catalyst may comprise one or a mixture of crystalline molecular sieves having the structure of zeolite Beta, zeolite Y, mordenite or an MCM-22 family material having an X-ray diffraction pattern including d-spacing maxima at 12.4±0.25, 6.9±0.15, 3.57±0.07 and 3.42±0.07 Angstroms.

The X-ray diffraction data used to characterize said above catalyst structures are obtained by standard techniques using the K-alpha doublet of copper as the incident radiation and a diffractometer equipped with a scintillation counter and associated computer as the collection system. Materials having the above X-ray diffraction lines include, for example, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in U.S. Pat. No. 6,231,751), ITQ-30 (described in WO 2005-118476), MCM-36 (described in U.S. Pat. No. 5,250,277), MCM-49 (described in U.S. Pat. No. 5,236,575) and MCM-56 (described in U.S. Pat. No. 5,362,697), with MCM-22 being particularly preferred.

Zeolite Beta is disclosed in U.S. Pat. No. 3,308,069. Zeolite Y and mordenite occur naturally but may also be used in one of their synthetic forms, such as Ultrastable Y (USY), which is disclosed in U.S. Pat. No. 3,449,070, Rare earth exchanged Y (REY), which is disclosed in U.S. Pat. No. 4,415,438, and TEA-mordenite (i.e., synthetic mordenite prepared from a reaction mixture comprising a tetraethylammonium directing agent), which is disclosed in U.S. Pat. Nos. 3,766,093 and 3,894,104. However, in the case of TEA-mordenite for use in the transalkylation catalyst, the particular synthesis regimes described in the patents noted lead to the production of a mordenite product composed of predominantly large crystals with a size greater than 1 micron and typically around 5 to 10 micron. It has been found that controlling the synthesis so that the resultant TEA-mordenite has an average crystal size of less than 0.5 micron results in a transalkylation catalyst with materially enhanced activity for liquid phase aromatics transalkylation.

The small crystal TEA-mordenite desired for transalkylation can be produced by crystallization from a synthesis mixture having a molar composition within the following ranges in Table 3C below:

TABLE 3C

|  | Useful | Preferred |
|---|---|---|
| $R/R^+Na^+$ = | >0.4 | 0.45-0.7 |
| $OH^-/SiO_2$ = | <0.22 | 0.05-0.2 |
| $Si/Al_2$ = | >30-90 | 35-50 |
| $H_2O/OH$ = | 50-70 | 50-60 |

The crystallization of small crystal TEA-mordenite from this synthesis mixture is conducted at a temperature of 90° C. to 200° C., for a time of 6 to 180 hours.

EXAMPLES

Non-limiting examples of the invention involving an improved alkylation mechanism are described with reference to the following experiments. In these experiments, catalyst reactivity was measured by the following procedure.

Equipment

A 300 ml Parr batch reaction vessel equipped with a stir rod and static catalyst basket was used for the activity and selectivity measurements. The reaction vessel was fitted with two removable vessels for the introduction of benzene and propylene respectively.

Feed Pretreatment

Benzene

Benzene was obtained from a commercial source. The benzene was passed through a pretreatment vessel (2 L Hoke vessel) containing 500 cc. of molecular sieve 13×, followed by 500 cc. of molecular sieve 5A, then 1000 cc. of Selexsorb CD, then 500 cc. of 80 wt. % MCM-49 and 20 wt. % $Al_2O_3$. All feed pretreatment materials were dried in a 260° C. oven for 12 hours before using.

Propylene

Propylene was obtained from a commercial specialty gases source and was polymer grade. The propylene was passed through a 300 ml vessel containing pretreatment materials in the following order:
  a. 150 ml molecular sieve 5A
  b. 150 ml Selexsorb CD
Both guard-bed materials were dried in a 260° C. oven for 12 hours before using.

Nitrogen

Nitrogen was ultra high purity grade and obtained from a commercial specialty gases source. The nitrogen was passed through a 300 ml vessel containing pretreatment materials in the following order:
  a. 150 ml molecular sieve 5A
  b. 150 ml Selexsorb CD
Both guard-bed materials were dried in a 260° C. oven for 12 hours before using.

Catalyst Preparation and Loading

A 2 gram sample of catalyst was dried in an oven in air at 260° C. for 2 hours. The catalyst was removed from the oven and immediately 1 gram of catalyst was weighed. Quartz chips were used to line the bottom of a basket followed by loading of 0.5 or 1.0 gram of catalyst into the basket on top of the first layer of quartz. Quartz chips were then placed on top of the catalyst. The basket containing the catalyst and quartz chips was placed in an oven at 260° C. overnight in air for about 16 hours.

The basket containing the catalyst and quartz chips was removed from the oven and immediately placed in the reactor and the reactor was immediately assembled.

Test Sequence

The reactor temperature was set to 170° C. and purged with 100 sccm (standard cubic centimeter) of the ultra high purity nitrogen for 2 hours. After nitrogen purged the reactor for 2 hours, the reactor temperature was reduced to 130° C., the nitrogen purge was discontinued and the reactor vent closed. A 156.1 gram quantity of benzene was loaded into a 300 ml transfer vessel, performed in a closed system. The benzene vessel was pressurized to 2169 kPa-a (300 psig) with the ultra high purity nitrogen and the benzene was transferred into the reactor. The agitator speed was set to 500 rpm and the reactor was allowed to equilibrate for 1 hour. A 75 ml Hoke transfer vessel was then filled with 28.1 grams of liquid propylene and connected to the reactor vessel, and then connected with 2169 kPa-a (300 psig) ultra high purity nitrogen. After the one-hour benzene stir time had elapsed, the propylene was transferred from the Hoke vessel to the reactor. The 2169 kPa-a (300 psig) nitrogen source was maintained connected to the propylene vessel and open to the reactor during the entire run to maintain constant reaction pressure during the test. Liquid product samples were taken at 30, 60, 90, 120, and 180 minutes after addition of the propylene.

In the Examples below, selectivity is the weight ratio of recovered product diisopropylbenzene to recovered product isopropylbenzene (DIPB/IPB) after propylene conversion reached 99+%. The activity of all examples is determined by calculating the 2nd order rate constant for a batch reactor using mathematical techniques known to those skilled in the art.

Example 1

Sixteen parts water and 1 part 45% sodium aluminate solution (22% $Al_2O_3$, 19.5% $Na_2O$), were charged to an autoclave reactor. The solution was agitated at 60 rpm for 1 to 24 hours at ambient temperature. Then 3.14 parts $SiO_2$ (Ultrasil-VN3PM-Modified, now known as Sipernat 320C and obtainable from Evoniks, formerly Degussa) and 0.02 part MCM-56 seeds (drycake) were added to form the first reaction mixture. The reactor was sealed and pressure tested. Then 0.53 part hexamethyleneimine (HMI as 100% organic) was charged to the reactor to form the second reaction mixture. The second reaction mixture was agitated at 50 rpm for less than 48 hours at ambient temperature. The reactor was then heated to 151° C. at 50 rpm and the contents were allowed to crystallize for 28 hours forming a resulting mixture. The resulting mixture comprised MCM-56 and less than 10 wt. % impurity as confirmed by X-ray diffraction. The reactor was cooled to 127° C. and the organic removed via the HMI/water azeotrope, i.e., "flashed", into a collection vessel. The flashed solvent ("condensate") was collected for recycle by combining with additional fresh HMI for subsequent batches. The reactor was cooled and the product discharged. The extent of crystallization was confirmed by BET surface area. Formulation particulars and results for this Example 1 are reported in Tables 4 and 5 below.

Example 1.1

Sixteen parts water, 1 part 45% sodium aluminate solution (22% $Al_2O_3$, 19.5% $Na_2O$), 3.13 parts $SiO_2$ (Sipernat 320C), 0.02 part MCM-56 seeds, and 0.53 part hexamethyleneimine (HMI as 100% organic) were charged to an autoclave reactor. The reactor was sealed and pressure tested. The resulting solution was agitated at 250 rpm for less than 48 hours at ambient temperature. The autoclave was then heated to 151° C. at 250 rpm and the contents were allowed to react for 72 hours. At that time it was confirmed by X-ray diffraction that the product was amorphous. The reactor was cooled to 127° C. and the organic removed via the HMI/water azeotrope, i.e., "flashed", into a collection vessel. The reactor was cooled and the product discharged. The lack of crystallization was confirmed by BET surface area. Formulation particulars and results for this Example 1.1 are reported in Tables 4 and 5 below.

Example 1.2

Sixteen parts water, 1 part 45% sodium aluminate solution (22% $Al_2O_3$, 19.5% $Na_2O$), 3.14 parts $SiO_2$ (Sipernat 320C) and 0.02 part MCM-56 seeds (drycake) were charged to an autoclave reactor to form the first reaction mixture, and then 0.53 part hexamethyleneimine (HMI as 100% organic) was charged to the reactor to form the second reaction mixture. The reactor was sealed and pressure tested. The second reaction mixture was agitated at 250 rpm for less than 48 hours at ambient temperature. The reactor was heated to 151° C. at 250 rpm and the contents were allowed to crystallize for 72 hours forming a resulting mixture. The resulting mixture comprised MCM-56 and less than 10 wt. % impurity as confirmed by X-ray diffraction. The reactor was cooled to 127° C. and the organic removed via the HMI/water azeotrope, i.e., "flashed", into a collection vessel. The reactor was cooled and the product discharged. For some crystals, the extent of crystallization was confirmed by BET surface area. Formulation particulars and results for this Example 1.2 are reported in Tables 4 and 5 below.

Example 2

Sixteen parts water and 1 part 45% sodium aluminate solution (22% $Al_2O_3$, 19.5% $Na_2O$), were charged to an autoclave reactor. The solution was agitated at 60 rpm for 1 to 24 hours at ambient temperature. Then 3.14 parts $SiO_2$ (Sipernat 320C) and 0.02 part MCM-56 seeds (drycake) were added to form the first reaction mixture. The reactor was sealed and pressure tested. Then 0.53 part hexamethyleneimine (HMI as 100% organic) was charged to the reactor to form the second reaction mixture. The second reaction mixture was agitated at 50 rpm for less than 48 hours at ambient temperature. The reactor was sealed, heated to 141.5° C. at 50 rpm and the contents were allowed to crystallize for 36 hours forming a resulting mixture. The resulting mixture comprised MCM-56 and less than 10 wt. % impurity as confirmed by X-ray diffraction. The reactor was cooled to 127° C. and the organic removed via the HMI/water azeotrope, i.e., "flashed", into a collection vessel. The flashed solvent ("condensate") was collected for recycle by combining with additional fresh HMI for subsequent batches. The reactor was cooled and the product discharged. The extent of crystallization was confirmed by BET surface area. Formulation particulars and results for this Example 2 are reported in Tables 4 and 5 below.

Example 3

To approximately 0.02 part MCM-56 seeds in the as-synthesized condition, left in the reactor from a previous MCM-56 crystallization, was added 0.72 part water and 1 part 5% USALCO, a sodium aluminate solution (as-received solution diluted with additional water from the original 22% $Al_2O_3$ and 19.5% $Na_2O$ to be 2.9% $Al_2O_3$ and 1.8% $Na_2O$) in an autoclave reactor. The solution was agitated at 60 rpm for 1 to 24 hours at ambient temperature. Then 0.31 part $SiO_2$ (Sipernat 320C) was added to form the first reaction mixture. The reactor was sealed and pressure tested. Then 0.053 part hexamethyleneimine (HMI as 100% organic) was charged to the reactor to form the second reaction mixture. The second reaction mixture was agitated at 60 rpm for less than 48 hours at ambient temperature. The reactor was sealed, heated to 148.5° C. at 60 rpm and the contents were allowed to crystallize for 36 hours forming a resulting mixture. The resulting mixture comprised MCM-56 and less than 10 wt. % impurity as confirmed by X-ray diffraction. The reactor was cooled to 127° C. and the organic removed via the HMI/water azeotrope, i.e., "flashed", into a collection vessel. The flashed solvent ("condensate") was collected for recycle by combining with additional fresh HMI for subsequent batches. The reactor was cooled and the product discharged. The extent of crystallization was confirmed by BET surface area. Formulation particulars and results for this Example 3 are reported in Tables 4 and 5 below.

Example 3.1

To 0.702 parts water was added 1 part 5% sodium aluminate obtainable from USALCO (as-received solution diluted with additional water from the original 22% $Al_2O_3$ and 19.5% $Na_2O$ to be 2.9% $Al_2O_3$ and 1.8% $Na_2O$) in an autoclave reactor. The solution was agitated at 60 rpm for 1 to 24 hours at ambient temperature. Then 0.31 part $SiO_2$ (Sipernat 320C) was added to form a first reaction mixture, but without seed crystals. The reactor was sealed and pressure tested. Then 0.053 part hexamethyleneimine (HMI as 100% organic) was charged to the reactor to form the second reaction mixture. The second reaction mixture was agitated at 60 rpm for less than 48 hours at ambient temperature. The reactor was sealed, heated to 148.5° C. at 60 rpm and the contents were allowed to crystallize for 61 hours. MCM-56 was confirmed by X-ray diffraction. The reactor was cooled to 127° C. and the organic removed via the HMI/water azeotrope, i.e., "flashed", into a collection vessel. The flashed solvent ("condensate") was collected for recycle by combining with additional fresh HMI for subsequent batches. The reactor was cooled and the product discharged. The extent of crystallization was confirmed by BET surface area. Formulation particulars and results for this Example 3.1 are reported in Tables 4 and 5 below.

Example 4

To approximately 0.02 part MCM-56 seeds in the as-synthesized condition, left in the reactor from previous MCM-56 crystallization, was added 0.72 part water and 1 part 5% USALCO (as-received solution diluted with additional water from the original 22% $Al_2O_3$ and 19.5% $Na_2O$ to be 2.9% $Al_2O_3$ and 1.8% $Na_2O$) in an autoclave reactor. The solution was agitated at 60 rpm for 1 to 24 hours at ambient temperature. Then 0.32 part $SiO_2$ (Sipernat 320C) was added to form the first reaction mixture. The reactor was sealed and pressure tested. Then 0.17 part hexamethyleneimine (HMI as 100% organic) was charged to the reactor to form the second reaction mixture. The second reaction mixture was agitated at 60 rpm for less than 48 hours at ambient temperature. The reactor was sealed, heated to 141.5° C. at 60 rpm and the contents were allowed to crystallize for 33 hours, at which time crystallization was stopped due to the resulting mixture not progressing to full crystallization. The reactor was cooled to 127° C. and the organic removed via the HMI/water azeotrope, i.e., "flashed", into a collection vessel. The reactor was cooled and the product discharged. The lack of crystallization was confirmed by BET surface area. Formulation particulars and results for this Example 4 are reported in Tables 4 and 5 below.

Example 4.1

One part 5% USALCO (as-received solution diluted with additional water from the original 22% $Al_2O_3$ and 19.5% $Na_2O$ to be 2.9% $Al_2O_3$ and 1.8% $Na_2O$) and 0.72 part water were charged to an autoclave reactor. Then 0.32 part $SiO_2$ (Sipernat 320C) was added. The reactor was sealed and pressure tested. The solution was agitated at 60 rpm for 1 to 24 hours at ambient temperature. Then 0.17 part hexamethyleneimine (HMI as 100% organic) was charged to the reactor to form the second reaction mixture. The second reaction mixture was agitated at 60 rpm for less than 48 hours at ambient temperature. The reactor was sealed, heated to 141.5° C. at 60 rpm and the contents were allowed to crystallize for 69 hours. At that time crystallization to MCM-56 was confirmed by X-ray diffraction, the reactor was cooled to 127° C. and the organic removed via the HMI/water azeotrope, i.e., "flashed", into a collection vessel. The reactor was cooled and the product discharged. The extent of crystallization was confirmed by BET surface area. Formulation particulars and results for this Example 4.1 are reported in Tables 4 and 5 below.

Example 5

Sixteen parts water and 1 part 45% sodium aluminate solution (22% $Al_2O_3$, 19.5% $Na_2O$), were charged to an autoclave reactor. The solution was agitated between 60 and 250 rpm for 1 to 24 hours at ambient temperature. Then 3.43 parts $SiO_2$ (Sipernat 320C) was added to the reactor. The reactor was sealed and pressure tested. Then 0.53 parts hexamethyleneimine (HMI as 100% organic) were charged to the reactor to form the second reaction mixture. The second reaction mixture was agitated at 60 rpm for less than 48 hours at ambient temperature. The reactor was sealed, heated to 148.5° C. at 60 rpm and the contents were allowed to crystallize for 56 hours. At that time crystallization to MCM-56 was confirmed by X-ray diffraction, the reactor was cooled to 127° C. and the organic removed via the HMI/water azeotrope, i.e., "flashed", into a collection vessel. The reactor was cooled and the product discharged. The extent of crystallization was confirmed by BET surface area. Formulation particulars and results for this Example 5 are reported in Tables 4 and 5 below.

TABLE 4

| Example | $SiO_2$/$Al_2O_3$ | $OH/SiO_2$ | $H_2O/SiO_2$ | $R/SiO_2$ | $M/SiO_2$ | Seeds* |
|---|---|---|---|---|---|---|
| 1 | 19 | 0.12 | 19 | 0.11 | 0.14 | 1.0 |
| 1.1 | 19 | 0.12 | 19 | 0.11 | 0.14 | 0.0 |
| 1.2 | 19 | 0.12 | 19 | 0.11 | 0.14 | 1.0 |
| 2 | 19 | 0.12 | 19 | 0.11 | 0.14 | 1.0 |
| 3 | 17 | 0.11 | 18 | 0.11 | 0.13 | 1.0 |
| 3.1 | 17 | 0.11 | 18 | 0.11 | 0.13 | 0.0 |
| 4 | 17 | 0.11 | 19 | 0.34 | 0.12 | 1.0 |
| 4.1 | 17 | 0.11 | 19 | 0.36 | 0.12 | 0.0 |
| 5 | 21 | 0.11 | 17 | 0.10 | 0.13 | 0.0 |

*Seeds in weight percent based on the weight of the crystals recovered from the reaction mixture.

TABLE 5

| Example | Temperature, ° C. | Stir Rate, rpm | Time** |
|---|---|---|---|
| 1 | 151 | 50 | 28 |
| 1.1 | 151 | 250 | 72 (amorphous) |
| 1.2 | 151 | 250 | 72 |
| 2 | 141.5 | 50 | 36 |
| 3 | 148.5 | 60 | 36 |
| 3.1 | 148.5 | 60 | 61 |
| 4 | 141.5 | 60 | 33 (not fully crystallized) |
| 4.1 | 141.5 | 60 | 69 (very slow) |
| 5 | 148.5 | 60 | 56 |

**Time in hours until crystallization is complete or not progressing.

It is observed from Example 1.1 that the first reaction mixture without the required MCM-56 seed crystals to form a second reaction mixture, even at higher sheer and the same temperature, did not crystallize in over 2.5 times the crystallization time for Example 1. Example 1.2 shows that repeating Example 1.1 except with a first reaction mixture comprising the seeds provides crystalline MCM-56. Example 3 shows that order of seed addition for the first reaction mixture does not adversely affect the outcome, and that the MCM-56 seeds may be as-synthesized. Example 3.1 compared to Example 3 demonstrates that crystallization is significantly slower without forming the first reaction mixture required of the present method. Example 4.1 compared to Example 4 demonstrates that crystallization is significantly slower without forming the first or second reaction mixture required of the present method.

Example 6

To formulate catalyst comprising "ex-situ seeded" MCM-56 manufactured by the present improved process, 40 parts MCM-56 product recovered from Example 1 (100% solids basis) was combined with 60 parts UOP Versal 300™ pseudo-boehmite alumina (100% solids basis). The combined dry powder was placed in a lab scale Lancaster Muller and mixed for 30 minutes. Sufficient water was added during the mixing to produce an extrudable paste. The extrudable paste was formed into 1/20" quadrulobe extrudate using a 2 inch laboratory Bonnot extruder. The extrudate was dried overnight at 121° C. in an oven. The dried extrudate was heated at a rate of 2.4° C. per minute to 538° C. and held for 3 hours under flowing nitrogen. The extrudate was then cooled to ambient temperature and humidified with saturated air overnight. The humidified extrudate was exchanged with 5 milliliters of 1 N ammonium nitrate per gram of catalyst for 1 hour. The ammonium nitrate exchange was repeated with fresh ammonium nitrate. The ammonium exchanged extrudate was then washed with 5 volumes deionized water per volume of extrudate to remove residual nitrate. The washed extrudate was dried overnight in an oven at 121° C. The extrudate was then calcined in a nitrogen/air mixture at the following conditions. The extrudate was ramped from ambient temperature to 426° C. in a 1% $O_2$/99% $N_2$ mixture at a heating rate of 28° C. per hour and held at 426° C. for 3 hours. The temperature was then increased to 482° C. at a rate of 28° C. per hour and held at 482° C. for an additional 3 hours. At 482° C. the $O_2$ was increased in stages to 7.6% $O_2$. The extrudate was held at 482° C. in the 7.6% $O_2$/92.4% $N_2$ stream for an additional 3 hours. The temperature was then raised to 534° C. at a rate of 28° C. per hour. The percentage of $O_2$ was gradually increased to 12.6% $O_2$, and the extrudate was held at 534° C. in 12.6% $O_2$ for 12 hours. The extrudate was then cooled to room temperature.

The catalyst comprising MCM-56 manufactured in this Example 6 was characterized by measuring the BET surface area, concentration of sodium as determined by inductively coupled plasma (ICP) by a commonly known method. Alpha Activity (hexane cracking) was determined as described in U.S. Pat. No. 3,354,078.

Examples 7, 8, 9, and 10

Three additional catalysts were formulated as in Example 6, except that one comprised 60 wt. % MCM-56 and 40 wt. % alumina (Example 7), another comprised 80 wt. % MCM-56 and 20 wt. % alumina (Example 8), and another comprised 20 wt. % MCM-56 and 80 wt. % alumina (Example 9) and another comprised 65 wt. % MCM-56 and 35 wt. % alumina (Example 10). The catalysts comprising MCM-56 manufactured in these Examples were characterized by measuring the BET surface area, concentration of sodium as determined by ICP, and Alpha Test activity (hexane cracking) as it is commonly known in the patent literature.

Example 11

In similar fashion, a 60 wt. % MCM-56, 40 wt. % alumina catalyst was formulated according to Example 6 using "in-situ seeded" MCM-56 crystal prepared according to Example 3.

Example 12

In similar fashion, a 100 wt. % MCM-56, 0 wt. % alumina catalyst was formulated according to Example 6 using a "non-seeded" MCM-56 crystal prepared according to Example 5.

Example 13

In similar fashion, a 80 wt. % MCM-56, 20 wt. % alumina catalyst was formulated according to Example 6 using a "non-seeded" MCM-56 crystal prepared according to Example 5.

Example 14

In similar fashion, a 80 wt. % MCM-56, 20 wt. % alumina catalyst was formulated according to Example 6 using a "non-seeded" MCM-56 crystal prepared according to Example 5. 0.05 wt. % polyvinyl alcohol was used as an extrusion aid in the formulation process.

Example 15

To further test the catalysts of Examples 6 through 14, one-half (0.5) gram of extrudate catalyst was loaded in a wire mesh screen basket along with 12 grams of quartz chips. The basket and contents were dried overnight (~16 hours) in an oven at 260° C. The basket was then loaded in a 300 cc Parr autoclave. The autoclave was sealed and purged free of air with flowing nitrogen. The autoclave was heated to 170° C. and purged with 100 sccm of nitrogen for 2 hours. The autoclave agitator was set to 500 rpm. Then, 156.1 grams of benzene was transferred to the autoclave, and the temperature was set to 130° C. at an agitation speed of 500 rpm for 1 hour. After 1 hour, 28.1 grams of propylene was transferred to the autoclave using a 75 cc Hoke transfer vessel. A constant head pressure was maintained on the autoclave using a nitrogen blanket. Liquid product samples were taken at 30, 60, 90, 120 and 180 minutes. The liquid samples were analyzed on an Agilent 5890 GC. The GC data was fitted to a $2^{nd}$ order kinetic model. The $2^{nd}$ order kinetic rate constant for the conversion of benzene and propylene was calculated along with the ratio of diisopropylbenzene (DIPB) to cumene and triisopropylbenzene (TRIPB) to cumene at 3 hours time-on-stream.

Table 6 and FIGS. 1, 2, 3 and 4 summarize the physical and catalytic properties of the "ex-situ seeded" MCM-56 catalyst compositions (Examples 6 to 10), the "in-situ" seeded MCM-56 catalyst compositions (Example 11), and the "non-seeded" MCM-56 catalyst compositions (Examples 12 to 14).

Figure 2:
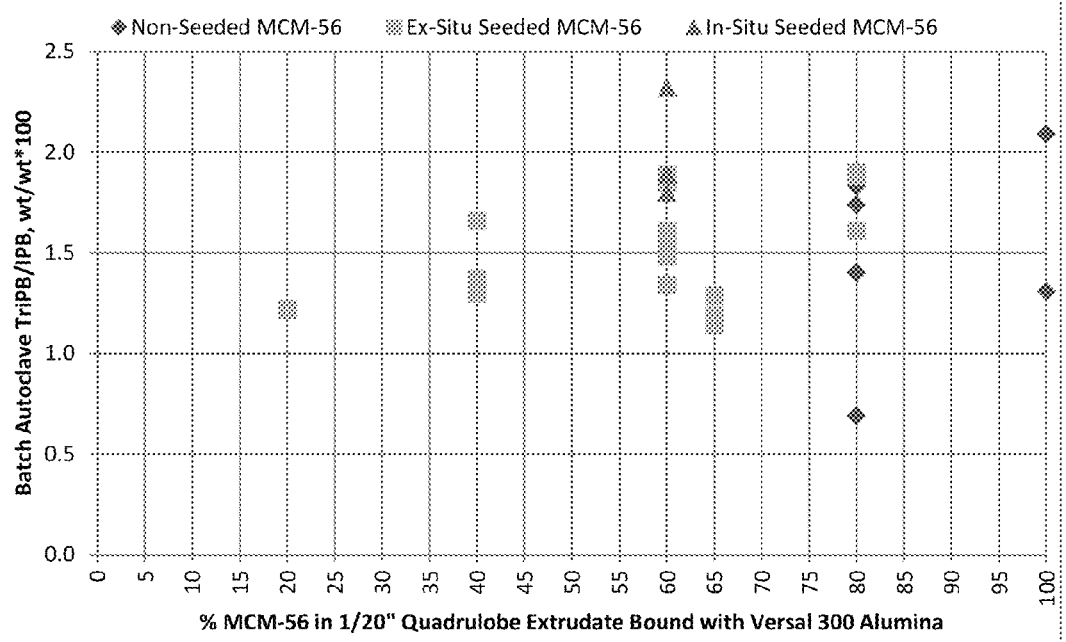
FIG. 2 shows a plot of triisopropylbenzene/isopropylbenzene selectivity (ordinate) versus the percentage of MCM-56 in the 1/20" quadrulobe extrudate bound with Versal 300 alumina (abscissa), for non-seeded MCM-56, ex-situ seeded MCM-56 and in-situ seeded MCM-56.
Figure 3:
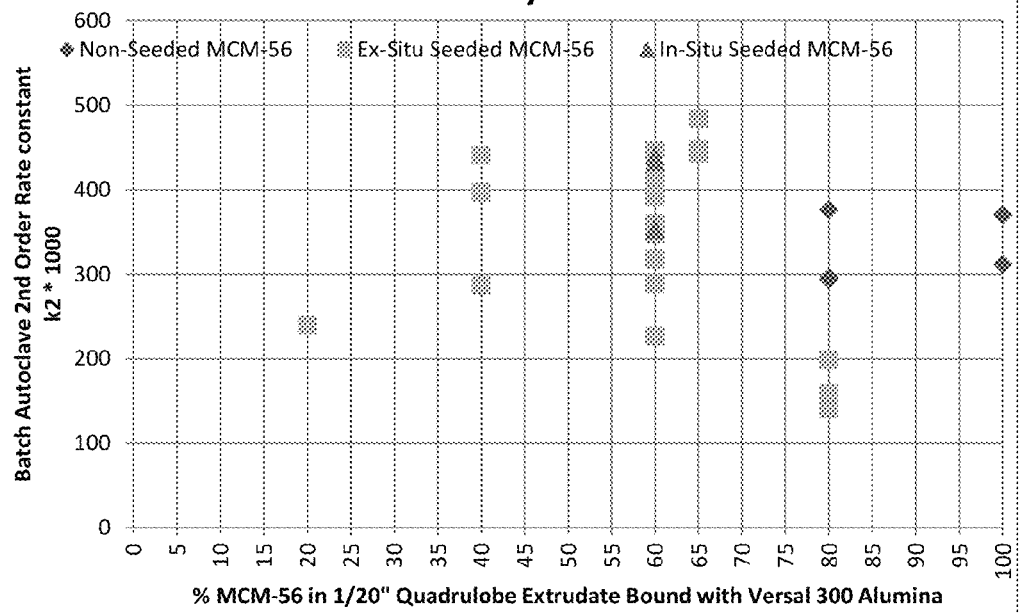
FIG. 3 shows a plot of activity (as a 2nd order rate constant $k_2$ times 1000) (ordinate) versus the percentage of MCM-56 in the 1/20" quadrulobe extrudate bound with Versal 300 alumina (abscissa), for non-seeded MCM-56, ex-situ seeded MCM-56 and in-situ seeded MCM-56.
Figure 4:
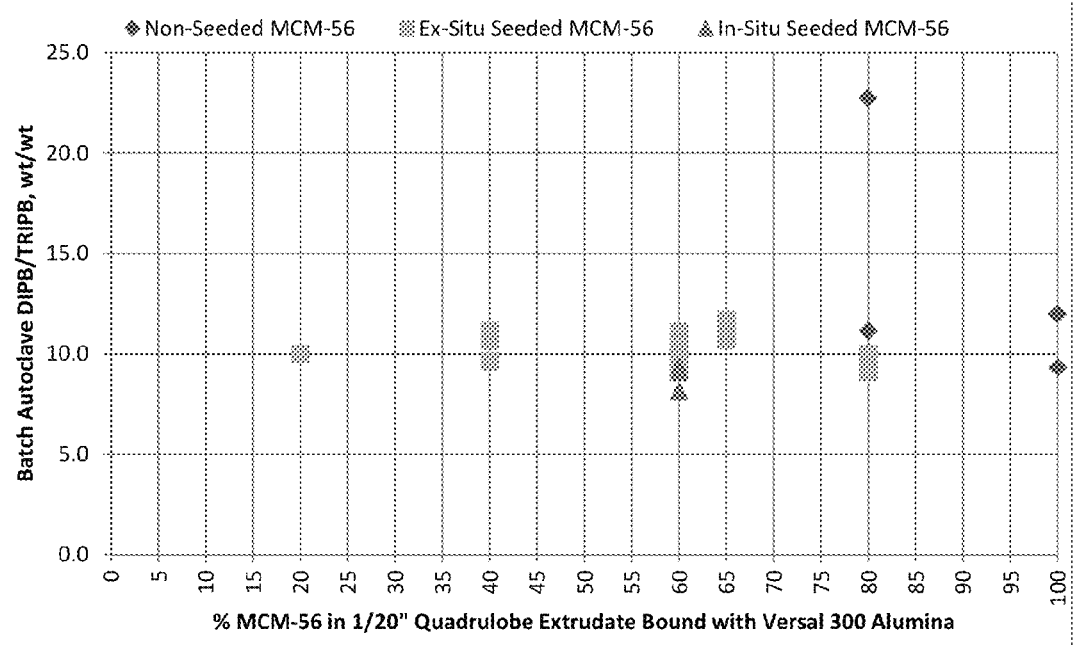
FIG. 4 shows a plot of diisopropylbenzene/triisopropylbenzene selectivity (ordinate) versus the percentage of MCM-56 in the 1/20" quadrulobe extrudate bound with Versal 300 alumina (abscissa), for non-seeded MCM-56, ex-situ seeded MCM-56 and in-situ seeded MCM-56.

FIG. 1 shows that the DIPB/IPB ratio generally decreases as the MCM-56 content in the extrudate decreases from 100% to 20%. FIG. 2 clearly shows that the heavy components (TRI-IPB's), which require an additional and difficult transalkylation reaction (in commercial operation) back to cumene, are reduced when the MCM-56 content is less than 80 wt. % and preferably less than 65 wt. % and most preferably less than 60 wt. %. FIG. 3 shows that we are able to maintain a 2nd order rate constant for the alkylation of propylene with benzene, $k_2$, greater than or equal to 0.20 even though the zeolite content is reduced from 100% to 20%. FIG. 4 shows that the ratio of DIPB/TRI-IPB is relatively constant over the range of MCM-56 content of 20 wt. % to 100 wt. %. All of the "ex-situ" seeded MCM-56 data in the Figures are in the Tables.

TABLE 6

| | Example 6 | | |
|---|---|---|---|
| MCM-56 (wt. %), Al$_2$O$_3$ (wt. %) | 40/60 | 40/60 | 40/60 |
| SODIUM (wt. %) | 0.0269 | 0.017 | 0.0215 |
| Alpha Activity | 230 | 300 | 220 |
| Rate Constant (1) | 287 | 441 | 397 |
| DIPB/Cumene (2) | 14.6 | 14.5 | 16 |
| TRIPB/Cumene (3) | 1.37 | 1.3 | 1.66 |
| TRIPB/DIPB | 0.09 | 0.09 | 0.10 |
| BET Surface Area (m$^2$/g) | 389 | 379 | 390 |
| Zeolite Surface Area (m$^2$/g) | 110 | 95 | 99 |
| Matrix Surface Area (m$^2$/g) | 279 | 284 | 290 |

| | Example 7 | | | |
|---|---|---|---|---|
| MCM-56 (wt. %), Al$_2$O$_3$ (wt. %) | 60/40 | 60/40 | 60/40 | 60/40 |
| SODIUM (wt. %) | NA | NA | 0.0362 | 0.0435 |
| Alpha Activity | 220 | NA | 240 | 270 |
| Rate Constant (1) | 0.318 | 0.358 | 360 | 0.414 |
| | 0.348 | 0.392 | | 0.447 |
| | 0.227 | 0.289 | | 0.439 |
| DIPB/Cumene (2) | 14.9 | 17.2 | 17 | 15.6 |
| | 15.7 | 15.4 | | 17.0 |
| | 16.4 | 16.0 | | 18.1 |
| TRIPB/Cumene (3) | 1.34 | 1.89 | 1.86 | 1.85 |
| | 1.51 | 1.59 | | 1.48 |
| | 1.58 | 1.61 | | 2.11 |
| TRIPB/DIPB | 0.09 | 0.11 | 0.11 | 0.12 |
| | 0.10 | 0.10 | | 0.09 |
| | 0.10 | 0.10 | | 0.12 |
| BET Surface Area (m$^2$/g) | 396 | 428 | 382 | 394 |
| Zeolite Surface Area (m$^2$/g) | 144 | 157 | 136 | 151 |
| Matrix Surface Area (m$^2$/g) | 252 | 271 | 246 | 243 |

| | Example 8 | Example 9 | Example 10 |
|---|---|---|---|
| MCM-56 (wt. %), Al$_2$O$_3$ (wt. %) | 80/20 | 20/80 | 65/35 |
| SODIUM (wt. %) | 0.0376 | NA | NA |
| Alpha Activity | 200 | 110 | 290 |
| Rate Constant (1) | 0.199 | 0.24 | 0.443 |
| | 0.141 | | 0.448 |
| | 0.160 | | 0.484 |
| DIPB/Cumene (2) | 16.1 | 12.2 | 12.2 |
| | 17.3 | | 14.4 |
| | 17.1 | | 13.9 |
| TRIPB/Cumene (3) | 1.61 | 1.22 | 1.14 |
| | 1.90 | | 1.29 |
| | 1.88 | | 1.19 |
| TRIPB/DIPB | 0.10 | 0.10 | 0.09 |
| | 0.11 | | 0.09 |
| | 0.11 | | 0.09 |
| BET Surface Area (m$^2$/g) | 435 | 342 | 425 |
| Zeolite Surface Area (m$^2$/g) | 212 | 34 | 171 |
| Matrix Surface Area (m$^2$/g) | 223 | 308 | 255 |

Example 16

MCM-56 zeolites were manufactured using the seeded zeolite synthesis, as described above in Example 1. The MCM-49 zeolite was also manufactured using seeds and formulated into catalyst as in Example 8. The catalysts comprising MCM-56 were formulated into catalysts as in Examples 16 to 19. These formulated catalysts were then placed in a testing apparatus to determine their selectivity for diethylbenzene (DEB) by-products (as measured by the sum of the diethylbenzenes divided by the ethylbenzene (EB)). The testing apparatus consisted of a feed system for supplying benzene (B) and ethylene (E); a mixing zone to ensure proper dissolution of the ethylene in the benzene; a reactor consisting of ½" stainless steel tubing; a heating element capable of maintaining a +/−4° C. linear temperature profile; an in-line sampling valve for automated sample collection; and a GC containing an FID for determining the relative amounts of hydrocarbon species present in the effluent. Approximately one gram of catalyst is packed in the reactor with a small particle size silicon carbide as a diluent to ensure good flow distribution. The reactor also contains a 1/16" internal thermal couple to determine the internal temperature profile (5 points). The temperature and pressure of the testing was set nominally to be 180° C. at the inlet of the reactor bed and about 500 psig at the outlet of the reactor bed. The benzene to ethylene mole ratio (B:E) was nominally set to 19. The total flow was adjusted to achieve conversions less than 100%. Five different catalysts were tested and the results are shown for Examples 16.1 through 16.5. The conversion is a measure of ethylene conversion (ethylene converted divided by ethylene fed).

Example 16.1

Figure 5:
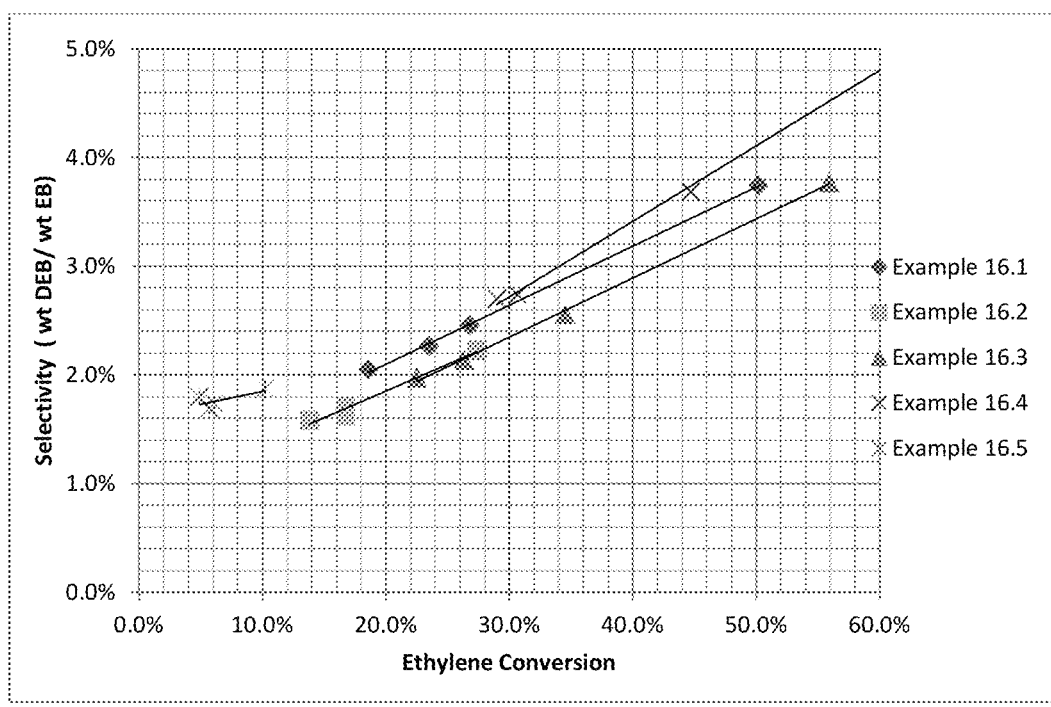
FIG. 5 shows a plot of the diethylbenzene/ethylbenzene selectivity (ordinate) versus the ethylene conversion (abscissa) for the processes of Examples 16.1-16.5.

In a comparative example, an 80 wt. % MCM-49, 20 wt. % alumina binder material was tested over a range of conversions. The selectivity is shown in FIG. 5 and Table 7.

Example 16.2

A 40 wt. % seeded MCM-56, 60 wt. % alumina binder material was tested over a range of conversions. The selectivity is shown in FIG. 5 and Table 7.

Example 16.3

A 60 wt. % seeded MCM-56, 40 wt. % alumina binder material was tested over a range of conversions. The selectivity is shown in FIG. 5 and Table 7.

Example 16.4

An 80 wt. % seeded MCM-56, 20 wt. % alumina binder material was tested over a range of conversions. The selectivity is shown in FIG. 5 and Table 7.

Example 16.5

A 20 wt. % seeded MCM-56, 80 wt. % alumina binder material was tested over a range of conversions. The selectivity is shown in FIG. 5 and Table 7.

TABLE 7

| | Ethylene Conversion | Selectivity (DEB/EB) | B:E (molar) | wt DEB/ wt EB |
|---|---|---|---|---|
| Ex. 16.1 | 50.2% | 0.035 | 20.33 | 3.7% |
| Ex. 16.1 | 26.8% | 0.025 | 18.66 | 2.5% |
| Ex. 16.1 | 18.6% | 0.0206 | 18.9 | 2.0% |
| Ex. 16.1 | 23.5% | 0.02266 | 19 | 2.3% |
| Ex. 16.2 | 27.4% | 0.02205 | 19.17 | 2.2% |
| Ex. 16.2 | 16.7% | 0.01787 | 18.16 | 1.7% |
| Ex. 16.2 | 13.8% | 0.0162 | 18.57 | 1.6% |
| Ex. 16.2 | 16.7% | 0.0166 | 18.6 | 1.6% |
| Ex. 16.3 | 55.9% | 0.034854 | 20.56 | 3.8% |
| Ex. 16.3 | 34.5% | 0.0254 | 19.12 | 2.6% |
| Ex. 16.3 | 22.5% | 0.0197 | 19.03 | 2.0% |
| Ex. 16.3 | 26.3% | 0.0212 | 19.14 | 2.1% |
| Ex. 16.4 | 61.8% | 0.04525 | 20.8 | 5.0% |
| Ex. 16.4 | 44.7% | 0.03611 | 19.4 | 3.7% |
| Ex. 16.4 | 29.0% | 0.02665 | 19.25 | 2.7% |
| Ex. 16.4 | 30.7% | 0.0269 | 19.35 | 2.7% |
| Ex. 16.5 | 10.2% | 0.019239 | 18.45 | 1.9% |
| Ex. 16.5 | 6.1% | 0.018582 | 17.67 | 1.7% |
| Ex. 16.5 | 4.9% | 0.019 | 18 | 1.8% |
| Ex. 16.5 | 5.7% | 0.0178 | 18 | 1.7% |

Table 7 Shows the selectivity for each example catalyst at different conversion levels. The selectivity is a measure of the sum of the DEB products divided by the EB product. It is also adjusted by the inverse proportion of the B:E ratio to ensure that the data is comparable.

FIG. 5 shows a plot of the ethylbenzene selectivity for each example versus the ethylene conversion. From this plot, several important conclusions can be drawn:

The seeded MCM-56 has a very high conversion compared to the MCM-49.

By lowering the zeolite content, some activity is sacrificed but with the advantage of lower selectivity of DEB by-products. Operation with this catalyst reduces utility consumption because less distillation is required with a lower DEB concentration.

The advantage of lower zeolite content is limited to a crystal/binder weight range below 80/20 and above 20/80 because, at or below the 20/80 level, the conversion is too low to be commercially useful (<10% compared to >10% for the rest of the catalysts).

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A process for producing a monoalkylated benzene comprising the step of contacting benzene with an alkylating agent in the presence of a catalyst composition under effective alkylation conditions to form said monoalkylated benzene and polyalkylated benzene, said catalyst composition comprising seeded MCM-56 and a binder, wherein the crystal/binder weight ratio in said catalyst composition is from about 20/80 to about 80/20, wherein said polyalkylated benzene comprises dialkylated benzene and trialkylated benzene, and the weight ratio of trialkylated benzene to dialkylated benzene is in the range from about 0.08 to about 0.12.

2. The process of claim 1, wherein said alkylation conditions include a temperature of from about 10° C. to about 260° C., a pressure from about 100 kPa-a to about 5500 kPa-a, a molar ratio of benzene to alkylating agent of from about 0.5:1 to about 10:1, and a feed weight hourly space velocity (WHSV) based on the alkylating agent of from about 0.5 hr$^{-1}$ to about 100 hr$^{-1}$.

3. The process of claim 1, wherein said alkylating agent is ethylene, and said monoalkylated benzene is ethylbenzene.

4. The process of claim 3, wherein said alkylation conditions include a temperature of from about 150° C. to about 300° C., a pressure up to about 20400 kPa-a, a weight hourly space velocity (WHSV) based on the ethylene of from about 0.1 hr$^{-1}$ to about 20 hr$^{-1}$, and a ratio of benzene to ethylene from about 0.5:1 to about 30:1 molar.

5. The process of claim 1, wherein said alkylating agent is propylene and said monoalkylated benzene is cumene.

6. The process of claim 5, wherein said alkylation conditions include a temperature of up to about 250° C., a pressure of about 25000 kPa-a or less, a weight hourly space velocity (WHSV) based on the propylene of from about 0.1 hr$^{-1}$ to about 250 hr$^{-1}$, and a ratio of benzene to propylene from about 0.5:1 to about 30:1 molar.

7. The process of claim 1, further comprising the step of contacting said polyalkylated benzene with additional benzene in the presence of a transalkylation catalyst to produce additional monoalkylated benzene.

8. The process of claim 7, wherein said transalkylation catalyst comprises at least one crystalline molecular sieve selected from the group consisting of zeolite Beta, zeolite Y, mordenite, an MCM-22 family material, and mixtures thereof.

9. The process of claim 8, wherein said MCM-22 family material has an X-ray diffraction pattern including d-spacing maxima at 12.4±0.25, 6.9±0.15, 3.57±0.07 and 3.42±0.07 Angstroms.

10. The process of claim 8, wherein said zeolite Y includes Ultrastable Y (USY) and Rare earth exchanged Y (REY).

11. The process of claim 8, wherein said mordenite includes TEA-mordenite.

12. The process of claim 1, wherein said binder is a synthetic or naturally occurring inorganic material selected from the group consisting of alumina, clay, silica and metal oxides.

13. A process for producing a monoalkylated benzene comprising the steps of:
(a) contacting benzene with an alkylating agent in the presence of a catalyst composition under effective alkylation conditions to form said monoalkylated benzene and polyalkylated benzene, said catalyst composition comprising seeded MCM-56 and a binder selected from the group consisting of alumina, clay, silica and/or metal oxides, wherein the crystal/binder weight ratio in said catalyst composition is from about 20/80 to about 80/20, wherein said polyalkylated benzene comprises dialkylated benzene and trialkylated benzene, and the weight ratio of trialkylated benzene to dialkylated benzene is in the range from about 0.08 to about 0.12; and
(b) contacting said polyalkylated benzene with additional benzene in the presence of a transalkylation catalyst to produce additional monoalkylated benzene, wherein said transalkylation catalyst comprises at least one crystalline molecular sieve selected from the group consisting of zeolite Beta, zeolite Y, mordenite, an MCM-22 family material, and mixtures thereof.

14. The process of claim 13, wherein said MCM-22 family material has an X-ray diffraction pattern including d-spacing maxima at 12.4±0.25, 6.9±0.15, 3.57±0.07 and 3.42±0.07 Angstroms.

15. The process of claim 13, wherein said alkylating agent is ethylene, said monoalkylated aromatic compound is ethylbenzene, said alkylation conditions include a temperature of from about 150° C. to about 300° C., a pressure up to about 20400 kPa-a, a weight hourly space velocity (WHSV) based on the ethylene of from about 0.1 hr$^{-1}$ to about 20 hr$^{-1}$, and a ratio of benzene to ethylene from about 0.5:1 to about 30:1 molar.

16. The process of claim 13, wherein said alkylating agent is propylene, said monoalkylated benzene is cumene, said alkylation conditions include a temperature of up to about 250° C., a pressure of about 25000 kPa-a or less, a weight hourly space velocity (WHSV) based on the ethylene of from about 0.1 hr$^{-1}$ to about 250 hr$^{-1}$, and a ratio of benzene to propylene from about 0.5:1 to about 30:1 molar.

17. The process of claim 13, wherein said crystalline molecular sieve of zeolite Y includes Ultrastable Y (USY) and Rare earth exchanged Y (REY).

18. The process of claim 13, wherein said crystalline molecular sieve of mordenite includes TEA-mordenite.

* * * * *